(12) United States Patent
Corma Canos et al.

(10) Patent No.: US 10,427,140 B2
(45) Date of Patent: Oct. 1, 2019

(54) ITQ-49 MATERIAL, METHOD FOR THE PRODUCTION THEREOF AND USE OF SAME

(71) Applicants: Avelino Corma Canos, Valencia (ES); Fernando Rey Garcia, Valencia (ES); Manuel Hernandez Rodriguez, Valencia (ES); Jose Luis Jorda Moret, Valencia (ES)

(72) Inventors: Avelino Corma Canos, Valencia (ES); Fernando Rey Garcia, Valencia (ES); Manuel Hernandez Rodriguez, Valencia (ES); Jose Luis Jorda Moret, Valencia (ES)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 2 days.

(21) Appl. No.: 15/678,636

(22) Filed: Aug. 16, 2017

(65) Prior Publication Data

US 2017/0368537 A1    Dec. 28, 2017

Related U.S. Application Data

(60) Division of application No. 14/516,743, filed on Oct. 17, 2014, now Pat. No. 9,764,311, which is a
(Continued)

(30) Foreign Application Priority Data

Apr. 18, 2012   (ES) .................................. 201230579

(51) Int. Cl.
*B01J 20/10* (2006.01)
*B01J 29/70* (2006.01)
(Continued)

(52) U.S. Cl.
CPC ........ *B01J 29/047* (2013.01); *B01D 53/0407* (2013.01); *B01D 53/8628* (2013.01);
(Continued)

(58) Field of Classification Search
CPC ........ C01B 39/48; C01B 37/005; B01J 29/70; B01J 20/10; B01J 20/3078; B01J 29/047;
(Continued)

(56) References Cited

U.S. PATENT DOCUMENTS 4,992,250 A    12/1991   Flanigen et al.
5,354,719 A *  10/1994   Gabelica ................. B01J 29/04
                                                          423/704
(Continued)

OTHER PUBLICATIONS

Robson, ed., Verified Synthesis of Zeolitic Materials, 2nd revised edition, 2001 (Year: 2001).*
(Continued)

*Primary Examiner* — David M Brunsman
(74) *Attorney, Agent, or Firm* — Priya G. Prasad

(57) ABSTRACT

The present invention refers to a microporous crystalline material, to the method for the production thereof and to the use of same, the material having a composition:

$$xX_2O_3 \colon zZO_2 \colon yYO_2$$

in which: X is a trivalent element such as Al, B, Fe, In, Ga, Cr, or mixtures thereof, where (y+z)/x can have values of between 9 and infinity; Z corresponds to a tetravalent element selected from Si, Ge or mixtures thereof; and Y corresponds to a tetravalent element such as Ti, Sn, Zr, V or mixtures thereof, where z/y can have values of between 10 and infinity.

27 Claims, 2 Drawing Sheets

Related U.S. Application Data continuation of application No. PCT/ES2013/000094, filed on Apr. 18, 2013.

(51) Int. Cl.

| | |
|---|---|
| *C01B 39/48* | (2006.01) |
| *B01D 53/86* | (2006.01) |
| *C07C 1/22* | (2006.01) |
| *B01J 29/04* | (2006.01) |
| *B01J 35/00* | (2006.01) |
| *B01D 53/04* | (2006.01) |
| *B01J 20/30* | (2006.01) |
| *C10G 73/02* | (2006.01) |
| *C01B 37/00* | (2006.01) |
| *C01B 39/54* | (2006.01) |
| *B01D 53/94* | (2006.01) |

(52) U.S. Cl.
CPC ........... *B01J 20/10* (2013.01); *B01J 20/3078* (2013.01); *B01J 29/70* (2013.01); *B01J 35/002* (2013.01); *C01B 37/005* (2013.01); *C01B 39/48* (2013.01); *C01B 39/54* (2013.01); *C07C 1/22* (2013.01); *C10G 73/02* (2013.01); *B01D 53/9418* (2013.01); *B01D 2253/108* (2013.01); *B01D 2255/50* (2013.01)

(58) Field of Classification Search
CPC ............... B01J 35/002; B01D 53/8628; B01D 53/9418; B01D 2253/108; B01D 2255/50; C07C 1/22; C10G 73/02
See application file for complete search history.

(56) References Cited

U.S. PATENT DOCUMENTS

| | | |
|---|---|---|
| 9,617,164 B2 | 4/2017 | Corcoran et al. |
| 9,764,311 B2 | 9/2017 | Corma Canos et al. |
| 2016/0008753 A1 | 1/2016 | Corcoran et al. |
| 2016/0008754 A1 | 1/2016 | Corcoran et al. |
| 2016/0008763 A1 | 1/2016 | Roderick et al. |
| 2016/0009618 A1 | 1/2016 | Corcoran et al. |

OTHER PUBLICATIONS

Burton et al., "The chemistry of phase selectivity in the synthesis of high-silica zeolites", Current Opinion in Colloid and Interface Science, Dec. 1, 2005, pp. 211-219, vol. 10, No. 5-6, Elsevier.

Simancas et al., "Modular Organic Structure-Directing Agents for the Synthesis of Zeolites", Science, Nov. 26, 2010, pp. 1219-1222, vol. 330.

Supplementary European Search Report based on Application No. 13778919.4-1375/2840064 PCT/ES2013000094 dated Jan. 11, 2016.

\* cited by examiner

ITQ-49 MATERIAL, METHOD FOR THE PRODUCTION THEREOF AND USE OF SAME

RELATED APPLICATIONS

The present application is a divisional application of co-pending U.S. application Ser. No. 14/516,743 filed Oct. 17, 2014. The present application claims the same priority as that claimed in co-pending U.S. application Ser. No. 14/516,743 filed Oct. 17, 2014.

FIELD OF THE INVENTION

This patent refers to a zeolitic material designated ITQ-49 and to the method of production thereof.

STATE OF THE ART, PRIOR TO THE INVENTION

Zeolites are porous crystalline aluminosilicates which have found important uses such as catalysts, ionic adsorbents and ionic exchangers. These zeolitic materials have well defined structures that form channels and cavities in their interior, with a uniform size and shape, what allows the adsortion of certain molecules, whereas they avoid that other molecules, with a too large size for spreading through the pores, pass into the interior of the crystal. This feature provides these materials with properties of a molecular sieve. These molecular sieves can include in their network, besides Si, other elements from the group IIIA of the perodic table, all of them being tetrahedrically coordinated. The negative charge generated by the elements of group IIIA tetrahedrically coordinated in network positions, is compensated by the presence of cations in the crystal, such as for example cations of alcaline or earth alcaline metals. These cations can be partially or totally exchanged by another cation type through ionic exchange techniques, thus varying the properties of a given silicate by selecting the desired cations.

Many zeolites have been synthesized in the presence of an organic molecule that acts as a structure directing agent. The organic molecules that act as a structure directing agent (SDA) usually contain nitrogen in their composition, and can give rise to organic cations stable in the reaction medium.

From the view points of the potential applications, the zeolites that contain channel systems with different pore apertures are especially desirable because they provide selectivity to the catalytic processes, said selectivities cannot be achieved with materials with channels with identical apertures in all of them. For these reasons a relevant scientific activity have been developed in this respect.

DESCRIPTION OF THE INVENTION

Figure 1:
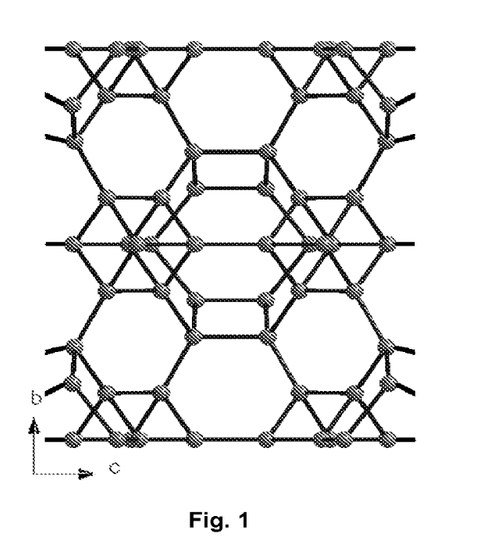
FIG. 1.—View of the zeolite ITQ-49 structure along a-axis (oxygen atoms are omitted for the shake of clarity).
Figure 2:
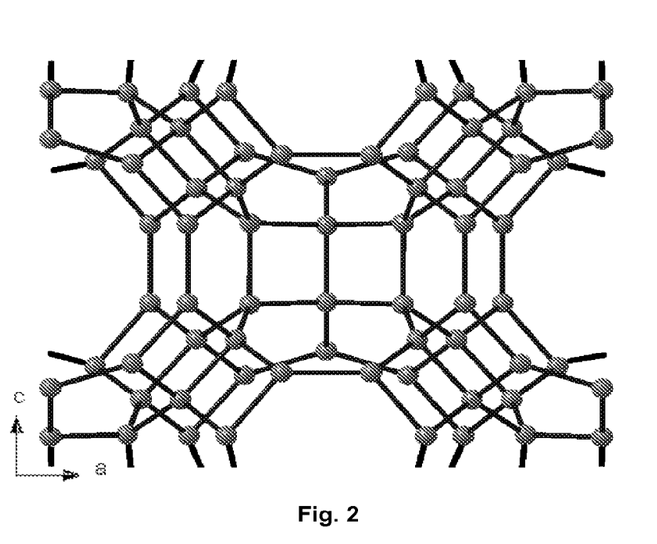
FIG. 2.—View of the zeolite ITQ-49 structure along b-axis (oxygen atoms are omitted for the shake of clarity).
Figure 3:
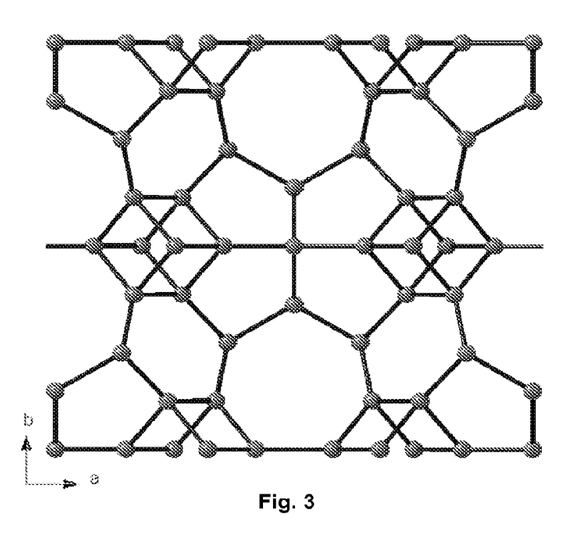
FIG. 3.—View of the zeolite ITQ-49 structure along c-axis (oxygen atoms are omitted for the shake of clarity).

The present invention describes a synthetic microporous crystalline material called ITQ-49. The structure of this material shows a microporous network made of channels with apertures formed by 7 and 8 $TO_4$ tetrahedra that crossed each other resulting in non-spherical cavities. These cavities can be entered through four windows formed 7 tetrahedra and two further windows formed by 8 tetrahedra, with a narrowing formed by 10 tetrahedra. These cavities are accessible to molecules of interest in the catalysis area, in adsorption or separation processes. Furthermore, it has structural units of a smaller size with a cube shape, that are not accessible because they only have windows formed by four tetrahedra. The structure of zeolite ITQ-49 can be described through its unit cell, that is the smallest structural unit that contains every structural elements of this material. The structure projections along the crystallographic axes are shown in FIGS. 1 to 3. Table 1 lists the atomic positions of all atoms in tetrahedral coordination in a unit cell. All these atoms are linked together through oxygen bridging atoms, that link adjacent tetrahedral atom pairs. Each unit cell contains 92 tetrahedrally coordinated atoms in total. Said atoms different from oxygen are designated T1, T2, T3, T4 to T92, are located in the crystallographic positions with Cartesian atomic coordinates x, y and z shown in Table 1.

TABLE 1

| Atomic Coordinates | a (Å) | b (Å) | c (Å) |
|---|---|---|---|
| T1 | 4.6 | 2.2 | 3.0 |
| T2 | 14.4 | 11.3 | 11.2 |
| T3 | 15.0 | 16.1 | 3.0 |
| T4 | 5.2 | 7.0 | 11.2 |
| T5 | 4.6 | 16.1 | 13.6 |
| T6 | 14.4 | 7.0 | 5.3 |
| T7 | 15.0 | 2.2 | 13.6 |
| T8 | 5.2 | 11.3 | 5.3 |
| T9 | 15.0 | 16.1 | 13.6 |
| T10 | 5.2 | 7.0 | 5.3 |
| T11 | 4.6 | 2.2 | 13.6 |
| T12 | 14.4 | 11.3 | 5.3 |
| T13 | 15.0 | 2.2 | 3.0 |
| T14 | 5.2 | 11.3 | 11.2 |
| T15 | 4.6 | 16.1 | 3.0 |
| T16 | 14.4 | 7.0 | 11.2 |
| T17 | 3.2 | 7.0 | 3.0 |
| T18 | 13.0 | 16.1 | 11.2 |
| T19 | 16.4 | 11.4 | 3.0 |
| T20 | 6.6 | 2.2 | 11.2 |
| T21 | 3.2 | 11.4 | 13.6 |
| T22 | 13.0 | 2.2 | 5.3 |
| T23 | 16.4 | 7.0 | 13.6 |
| T24 | 6.6 | 16.1 | 5.3 |
| T25 | 16.4 | 11.4 | 13.6 |
| T26 | 6.6 | 2.2 | 5.3 |
| T27 | 3.2 | 7.0 | 13.6 |
| T28 | 13.0 | 16.1 | 5.3 |
| T29 | 16.4 | 7.0 | 3.0 |
| T30 | 6.6 | 16.1 | 11.2 |
| T31 | 3.2 | 11.4 | 3.0 |
| T32 | 13.0 | 2.2 | 11.2 |
| T33 | 0.0 | 2.6 | 1.5 |
| T34 | 9.8 | 11.8 | 9.8 |
| T35 | 0.0 | 15.7 | 1.5 |
| T36 | 9.8 | 6.5 | 9.8 |
| T37 | 0.0 | 15.7 | 15.0 |
| T38 | 9.8 | 6.5 | 6.8 |
| T39 | 0.0 | 2.6 | 15.0 |
| T40 | 9.8 | 11.8 | 6.8 |
| T41 | 2.7 | 4.3 | 1.6 |
| T42 | 12.5 | 13.5 | 9.9 |
| T43 | 16.9 | 14.0 | 1.6 |
| T44 | 7.1 | 4.8 | 9.9 |
| T45 | 2.7 | 14.0 | 14.9 |
| T46 | 12.5 | 4.8 | 6.7 |
| T47 | 16.9 | 4.3 | 14.9 |
| T48 | 7.1 | 13.5 | 6.7 |
| T49 | 16.9 | 14.0 | 14.9 |
| T50 | 7.1 | 4.8 | 6.7 |
| T51 | 2.7 | 4.3 | 14.9 |
| T52 | 12.5 | 13.5 | 6.7 |
| T53 | 16.9 | 4.3 | 1.6 |
| T54 | 7.1 | 13.5 | 9.9 |
| T55 | 2.7 | 14.0 | 1.6 |
| T56 | 12.5 | 4.8 | 9.9 |
| T57 | 1.6 | 9.2 | 4.3 |
| T58 | 11.4 | 0.0 | 12.5 |
| T59 | 18.0 | 9.2 | 4.3 |

TABLE 1-continued

| Atomic Coordinates | a (Å) | b (Å) | c (Å) |
|---|---|---|---|
| T60 | 8.2 | 0.0 | 12.5 |
| T61 | 1.6 | 9.2 | 12.3 |
| T62 | 11.4 | 0.0 | 4.0 |
| T63 | 18.0 | 9.2 | 12.3 |
| T64 | 8.2 | 0.0 | 4.0 |
| T65 | 4.9 | 0.0 | 6.7 |
| T66 | 14.7 | 9.2 | 15.0 |
| T67 | 14.7 | 0.0 | 6.7 |
| T68 | 4.9 | 9.2 | 15.0 |
| T69 | 4.9 | 0.0 | 9.8 |
| T70 | 14.7 | 9.2 | 1.6 |
| T71 | 14.7 | 0.0 | 9.8 |
| T72 | 4.9 | 9.2 | 1.6 |
| T73 | 2.9 | 0.0 | 4.4 |
| T74 | 12.7 | 9.2 | 12.6 |
| T75 | 16.7 | 0.0 | 4.4 |
| T76 | 6.9 | 9.2 | 12.6 |
| T77 | 2.9 | 0.0 | 12.2 |
| T78 | 12.7 | 9.2 | 3.9 |
| T79 | 16.7 | 0.0 | 12.2 |
| T80 | 6.9 | 9.2 | 3.9 |
| T81 | 3.5 | 9.2 | 6.7 |
| T82 | 13.3 | 0.0 | 15.0 |
| T83 | 16.1 | 9.2 | 6.7 |
| T84 | 6.3 | 0.0 | 15.0 |
| T85 | 3.5 | 9.2 | 9.8 |
| T86 | 13.3 | 0.0 | 1.5 |
| T87 | 16.1 | 9.2 | 9.8 |
| T88 | 6.3 | 0.0 | 1.5 |
| T89 | 0.0 | 0.0 | 3.4 |
| T90 | 9.8 | 9.2 | 11.7 |
| T91 | 0.0 | 0.0 | 13.1 |
| T92 | 9.8 | 9.2 | 4.9 |

Each of the T atoms in Table 1 is surrounded by four oxygen atoms as first neighbours and four additional T atoms as second neighbours, in such a way that the T atoms are linked in pairs through oxygen bridges forming T-O-T bonds. The presence of cations or the different nature of the T atoms can modify the values shown on Table 1, so each crystallographic coordinate can be modified up to 1 Å with respect to the value given in Table 1

Zeolite ITQ-49 ha in its non calcined form an X ray diagram, the more important peaks of which are given in Table 2, and in Table 3 for its calcined form.

TABLE 2

| $2\theta^a$ | Relative intensity |
|---|---|
| 7.0 | w |
| 9.0 | vs |
| 9.7 | m |
| 10.7 | m |
| 11.5 | vw |
| 11.9 | vw |
| 12.6 | vw |
| 13.2 | w |
| 14.0 | w |
| 14.4 | vs |
| 15.2 | vw |
| 15.5 | vw |
| 16.7 | w |
| 17.1 | w |
| 17.5 | m |
| 18.0 | vw |
| 18.7 | vw |
| 19.4 | vw |
| 19.9 | vw |
| 20.6 | vw |
| 21.1 | vw |
| 21.5 | vw |
| 22.2 | vw |
| 22.7 | vw |
| 23.2 | w |
| 23.7 | vw |
| 24.0 | m |
| 24.8 | w |
| 25.4 | vw |
| 25.7 | vw |
| 26.0 | vw |
| 26.7 | vw |
| 27.3 | vw |
| 27.9 | vw |
| 28.4 | vw |
| 28.8 | vw |
| 29.1 | vw |
| 30.0 | vw |

$^a(\pm 0.5)$

TABLE 3

| $2\theta^a$ | Relative intensity |
|---|---|
| 7.0 | vs |
| 7.2 | vw |
| 9.0 | s |
| 9.6 | m |
| 10.7 | w |
| 11.5 | vw |
| 11.9 | w |
| 12.6 | vw |
| 13.2 | vw |
| 14.0 | vw |
| 14.4 | w |
| 15.2 | vw |
| 15.5 | vw |
| 16.8 | vw |
| 17.0 | vw |
| 17.5 | w |
| 18.0 | vw |
| 18.6 | vw |
| 19.4 | vw |
| 19.5 | vw |
| 19.9 | vw |
| 20.5 | vw |
| 21.1 | vw |
| 21.5 | vw |
| 22.2 | vw |
| 22.5 | vw |
| 23.3 | vw |
| 23.6 | vw |
| 24.0 | w |
| 24.7 | vw |
| 25.3 | vw |
| 25.7 | vw |
| 25.9 | vw |
| 26.5 | vw |
| 27.4 | vw |
| 27.9 | vw |
| 28.2 | vw |
| 28.4 | vw |
| 28.8 | vw |
| 29.1 | vw |
| 29.4 | vw |
| 29.9 | vw |

$^a(\pm 0.5)$

These X-ray difractograms were obtained with a Panalytical X'pert Pro diffractometer equipped with a slit of fixed divergence using copper $K_\alpha$ radiation. The relative intensity of the lines was calculated as the percentage relative to the most intense peak, and it considered as very strong (vs)=80-100, strong (s)=60-80, medium (m)=40-60, weak (w)=20-40, and very weak (vw)=0-20.

It must be taken into account that the listed diffraction data for these samples as simple or single lines, may be formed by multiple overlappings or superpositions of reflections that, under certain conditions, such as differences in the chemical composition, may appear as separated or partially separated lines. Generally, the changes in the chemical composition may cause variations in the parameters of the unit cell and/or changes in the crystal symmetry, without producing any change in the structure. These modifications, that also include changes in the relative intensities may also be due to differences in the kind and amount of compensating cations, network composition, size and shape of the crystals, preferred orientation or to the kind of thermal or hydrothermal treatments that they have undergone.

The present invention refers to a microporous crystalline material named ITQ-49, that can have a chemical composition:

$$xX_2O_3:yYO_2:zZO_2$$

wherein:
  X is a trivalent element selected from Al, B, fe, In, Ga, Cr, or mixtures thereof;
  Y is a tetravalent element selected from Ti, Sn, Zr, V, or mixtures thereof, preferably from Ti, Sn, Zr, or mixtures thereof;
  Z is a tetravalent element selected from Si, Ge or mixtures thereof, preferably Si;
  the value of (y+z)/x is comprised between 9 and infinity, preferably between 20 and infinity;
  the value of z/y is comprised between 10 and infinity, preferably between 15 and infinity.

From the given values, it is clearly deduced that the crystalline ITQ-49 material can be obtained in the absence of added trivalent elements.

According to a particular embodiment of the present invention, the value of x can be zero, therefore it can have a chemical composition:

$$yYO_2:zZO_2$$

According to another particular embodiment, the value of y is zero, therefore it can have a chemical composition:

$$xX_2O_3:zZO_2$$

where:
  the value of z/x is comprised between 9 and infinity, and more preferably between 20 and infinity.

According to a preferred embodiment, the material of the present invention, ITQ-49, has a chemical composition:

$$tP_2O_5:xX_2O_3:yYO_2:zZO_2$$

wherein:
  X is a trivalent element selected from Al, B, Fe, In, Ga, Cr, or mixtures thereof;
  Y is a tetravalent element selected from Ti, Sn, Zr, V, or mixtures thereof, preferably between Ti, Sn, Zr, or mixtures thereof;
  Z is a tetravalent element selected from Si, Ge, or mixtures thereof, preferably Si;
  P refers to phosphorus coming from the structure directing agent;
  the value of (y+z)/x is comprised between 9 and infinity, preferably between 20 and infinity;
  the value of z/y is comprised between 10 and infinity, preferably between 15 and infinity;
  the value of t(x+y+z) can be between 1 and 0.

From the given values, it is clearly deduced that the crystalline ITQ-49 material can be synthesized in the absence of added trivalent elements. The X-ray difractogram of the zeolite in its calcined form presents the diffraction peaks that are listed in Table 3.

According to a particular embodiment, x can be 0 and the ITQ-49 material can have a chemical composition:

$$tP_2O_5:yYO_2:zZO_2$$

wherein:
  t/(y+z) can be between 1 and 0.

According to another particular embodiment, y can be 0 and the ITQ-49 material can have a chemical composition:

$$tP_2O_5:xX_2O_3:zZO_2$$

wherein:
  The value of z/X is comprised between 9 and infinity, preferably between 20 and infinity.
  t/(x+z) can be between 1 and 0.

The calcined crystalline ITQ-49 material can be submitted to one or several processes of chemical extraction or washing in aqueous, alcoholic, organic media, or mixtures thereof to eliminate the inorganic residues $P_2O_5$ coming from the elimination of the structure directing agent. This treatment of extraction or washing can be performed in acidic, neutral or alkaline media.

According to a preferred embodiment, the material of the present invention, ITQ-49, have a chemical composition:

$$nR:xX_2O_3:zZO_2:yYO_2$$

wherein:
  X is a trivalent element selected from Al, B, Fe, In, Ga, Cr, or mixtures thereof;
  Y is a tetravalent element selected from Ti, Sn, Zr, V, or mixtures thereof, preferably from Ti, Sn, Zr, or mixtures thereof;
  Z is a tetravalent element selected from Si, Ge, or mixtures thereof, preferably Si;
  the value of (y+z)/x is comprised between 9 and infinity, preferably between 20 and infinity;
  The value of z/y is comprised between 10 and infinity, preferably between 15 and infinity;
  R is a structure directing agent, preferably said R contains P, more preferably R is a salt of an alkylphosphonium cation, and more preferably is selected between 1,4-butanediyl-bis(tritertbutyl)phosphonium hydroxide or one of its salts;
  the value of n/(x+y+z) is comprised between 1 and 0.001.

From the given values, it is clearly deduced that the crystalline ITQ-49 material can be synthesized in the absence of added trivalent elements. The ratio n/z can be between 1 and 0.001 in the ITQ-49 material as it is synthesized. The X-ray diffractogram of the zeolite in its synthesized form presents the diffraction peaks that are listed in Table 2.

According to a particular embodiment, x can be 0 and the ITQ-49 material can have a chemical composition:

$$nR:yYO_2:zZO_2$$

wherein:
  the value of n/(y+z) is comprised between 1 and 0.001.

According to an additional particular embodiment, y can be 0 and the ITQ-49 material can have a chemical composition:

$$nR:xX_2O_3:zZO_2$$

wherein:
  the value of z/x is comprised between 9 and infinity, preferably between 20 and infinity;
  the value of n/(x+z) is comprised between 1 and 0.001.

The cystalline ITQ-49 material calcined and/or calcined and washed can undergo one or several post-synthesis processes that incorporate or exchange trivalent elements using solutions that contain trivalent elements X, which can be selected from Al, Ga, B, Cr, Fe, In and mixtures thereof in aqueous, alcoholic, organic media or mixtures thereof. In this process, the inorganic residues $P_2O_5$, coming from the removal of the structure directing agent, can be eliminated. This treatment of incorporation of trivalent metals and/or washing can be performed in aqueous, neutral or alkaline media. The crystalline material, with incorporated trivalent metals through post-synthesis treatment, has a molar composition in its anhydrous state that is given by the equation:

$$xX_2O_3 : yYO_2 : zZO_2$$

wherein X is a trivalent element such as Al, B, Fe, In, Ga, Cr, or mixtures thereof, Y is a tetravalent element such as Ti, Sn, Zr, V, or mixtures thereof, and Z corresponds to an element selected from Si or Ge, or mixtures thereof. The value of $(y+z)/x$ is at least 9, and can be between 20 and infinity and the value of $z/y$ is at least 10. From the given values, it is clearly deduced that the crystalline material ITQ-49 can be synthesized in the absence of added trivalent elements. The X-ray diffractogram of the zeolite, after the post-synthesis treatment to incorporate trivalent elements in its structure, presents the characteristic diffraction peaks of ITQ-49 material.

The organic component present in the ITQ-49 material as synthesized can be eliminated, for example by extraction and/or by thermal treatment heating to a temperature above 200° C. for a time period that can be between 2 minutes and 25 hours.

The compensation cations in the material in its non-calcined form, or after a thermal treatment, can be exchanged, in the case of being present, by other metal cations, $H^+$ and precursors of $H^+$ for instance $NH_4^+$. Among the cations, that can be introduced by ionic exchange, those that can have a positive role in the activity of the material as catalyst are preferred, and cations such as H+, rare earth cations, and metals of group VIII are more specifically preferred, as well as elements of the groups IIA, IIIA, IVA, VA, IB, IIB, IIIB, IVB, VB, VIIB of the periodic table of the elements.

Also, it is possible to introduce cations in the network of ITQ-49 zeolite through post-synthesis treatments. These treatments consist of suspending the ITQ-49 sample, calcined or calcined and washed, in aqueous, alcoholic, organic solutions or a mixture thereof that contains the wanted trivalent element to be incorporated at a temperature between 0 and 200° C. for periods between 1 hour and 15 days.

With the object of preparing catalysts, the crystalline material of the present invention can be intimately combined with hydrogenating-dehydrogenating components such as platinum, palladium, nickel, rhenium, cobalt, tungsten, molybdenum, vanadium, chromium, manganese, iron and combinations thereof. The introduction of these elements can be carried out in the crystallization step, by exchange (if appropriate), and/or by impregnation or by physical mixing. These elements can be introduced in their cationic form and/or from salts or other compounds that by decomposition generate the metallic component or oxide in its suitable catalytic form.

Additionally, the present invention refers to the process for obtaining the ITQ-49 material described above.

According to the present invention, the preparation process of the ITQ-49 material can comprise at least a first step of preparation of a mixture that contains $H_2O$, a source of fluoride ions, an oxide or other source of tetravalent material Z and a structure directing agent (R), a source of the trivalent element X, an oxide or other source of the tetravalent material Y, wherein the synthesis mixture has a molar composition of oxides in the following ranges:

| | |
|---|---|
| $(YO_2 + ZO_2)/X_2O_3$ | higher than 2, preferably higher than 5. |
| $H_2O/(YO_2 + ZO_2)$ | 1-50, preferably 2-30. |
| $R/(YO_2 + ZO_2)$ | 0.05-3.0, preferably between 0.05-1. |
| $F^-/(YO_2 + ZO_2)$ | 0.01-3.0, preferably between 0.05-1. |
| $ZO_2/YO_2$ | higher than 5, preferably higher than 8-25. |
| $SiO_2/GeO_2$ | higher than 1, preferably higher than 5. |

A second step wherein the mixture can be kept at a temperature between 80 and 200° C. until crystals of the material are formed and a further step of recovery of the crystalline material.

According to a preferred embodiment of the present invention, Z is a mixture of Si and Ge.

According to another preferred embodiment, the structure directing agent R can be a compound that contains P, more preferably R is a salt of a alkylphosphonium cation, and more preferably is selected between 1,4-butanediyl-bis(tri-tertbutyl)phosphonium hydroxide or one of its salts.

This material can be prepared according to a particular embodiment, from a reaction mixture containing $H_2O$, a source of fluoride anions, optionally an oxide or a source of the trivalent element X, as for instance Al and/or B, an oxide or a source of the tetravalent element or elements Y, as for instance Si, a source of Ge, as for instance $GeO_2$ and an organic structure directing agent (R), generally an organic cation, which can contain atoms other than C, H and N in its composition. As structure directing agents compounds of alkylphosphonium kind, and more preferably 1,4-butanediyl-bis(tritertbutyl)phosphonium hydroxide or one of its salts, can be used.

The composition of the reaction mixture has the following composition in terms of molar relation of oxides:

| Reagents | Useful | Preferred |
|---|---|---|
| $(YO_2 + ZO_2)/X_2O_3$ | higher than 2 | higher than 5 |
| $H_2O/(YO_2 + ZO_2)$ | 1-50 | 2-30 |
| $R/(YO_2 + ZO_2)$ | 0.05-3.0 | 0.05-1.0 |
| $F^-/(YO_2 + ZO_2)$ | 0.01-3.0 | 0.05-1.0 |
| $ZO_2/YO_2$ | higher than 5 | 8-25 |
| $SiO_2/GeO_2$ | higher than 1 | higher than 5 |

The crystallization of the material can be carried out under stirring, in autoclaves at temperatures between 80 and 200° C., during enough time to achieve crystallization, for instance between 12 hours and 30 days.

Upon ending the crystallization step, the crystals of the material are separated from the mother liquor, and they are recovered. It must be taken into account that the components of the synthesis mixture can come from different sources, and, depending on these, the crystallization time and the crystallization conditions can vary. In order to facilitate the synthesis, crystals of the same material or of this calcined material, in amounts up to 15% in weight relative to the overall oxides, can be added as seeds to the synthesis mixture. These can be added previously or during crystallization.

According to a particular embodiment, the process of preparation of the ITQ-49 material can comprise a step of calcination of the obtained crystalline material, the calcination can be carried out under vacuum, in air, nitrogen, hydrogen, argon, helium or any other gas and at a temperature higher than 200 and lower than 1100° C., preferably between 200 and 1000° C., for a time that can be between 2 minutes and 25 hours. The ITQ-49 material, after calcination, has a system of pores free of organic matter, with an X-ray difractogram that has the peaks listed in Table 2. During this calcination, inorganic residues coming from the structure directing agent can stay inside the channels or on the surface of the material. These residues can be removed through a further washing treatment with water, any alcohol with at least six carbons, or mixtures thereof, as well as by aqueous or alcoholic solutions of inorganic salts.

According to a particular embodiment, such washing process or processes can comprise at least the following step:
a) suspension of the material in a solution of a compound selected from an acid, a base, an ammonium salt, a sodium salt, of any alkaline metal, any earth-alkaline metal or mixtures thereof. In a preferred manner, such solution is an aqueous, alcoholic, organic solution or mixture thereof.

The washing process is carried out at a temperature preferably comprised between 0° C. and 200° C. The diffraction diagram of the resulting material has the characteristic diffraction peaks of this ITQ-49 material.

Additionally, the calcined ITQ-49 material or the calcined and washed ITQ-49 material can undergo one or more post-synthesis treatments. Said treatments can preferably consist of treating ITQ-49 with aqueous, alcoholic, organic solutions or mixtures thereof, that contain trivalent elements X, selected preferably from Al, Ga, B, Cr, Fe, In, and mixtures thereof with the object of including them to the zeolitic network. This post-synthesis treatment can be performed at alkaline, acidic or neutral pHs at temperatures between 0 and 200° C. for a preferred time period between 1 hour to 15 days. The resulting material has the characteristic diffraction peaks of this ITQ-49 material.

After that, the washed solid can be recovered by filtration, centrifugation or any solid-liquid separation technique and it can be later activated through calcination at temperatures above 200° C.

According to a particular embodiment, the present invention refers to a process to obtain a material that has, additionally a post-synthesis treatment comprised, at least:
a) suspending the material in a solution that contains at least a trivalent element X selected from Al, Ga, B, Cr, Fe, In or mixtures thereof;
b) recovering the solid through filtration, centrifugation or any technique for separating solids and liquids;
c) activating the material through calcination at temperatures above 200° C.

In a preferred manner, the solution is selected from an aqueous, alcoholic, organic solutions or mixtures thereof. Additionally, such post-synthesis treatment is carried at a preferred temperature between 0 and 200° C.

The ITQ-49 material can be used as catalyst in process of conversion of hydrocarbons, alcohols to others of higher added value, in the removal of nitrogenated compounds from gas or liquid streams as well as in separation processes.

According to a particular embodiment, the ITQ-49 material can be used as catalyst in processes of hydrocarbon conversion, in processes of dewaxing of hydrocarbons, in processes of conversion of alcohols, in processes of conversion of alcohols with less than four carbons into olefins, in processes of removal of nitrogenated pollutants in gas or liquid streams, in processes of removal of nitrogen oxides in gas streams, in processes of removal of nitrogen oxides from gas streams in the presence of reducing agents, in processes of removal of nitrogen oxides from gas streams in the presence of ammonia as reducing agent, in processes of removal of nitrogen oxides in the presence of hydrocarbon as reducing agents and combinations thereof.

According to an additional particular embodiment, the ITQ-49 material can be used as adsorbent. In a preferred manner, it can be used as selective adsorbent in processes of separation of $CO_2$ and methane, in processes of separation of propane and propene, in processes of separation of linear olefins of the C4 fraction, and combinations thereof.

EXAMPLES

Example 1—Preparation of 1,4-butanediyl-bis(tritertbutyl)phosphonium hydroxide 20.2 g of tri-tertbutylphosphine are dissolved in 250 mL of acetonitrile. To this solution a solution of 61.5 g of 1,4-diiodobutane in 150 mL of acetonitrile was slowly added. The mixture was kept under stirring at 90° C. for 12 hours and then it is cooled down to room temperature.

The resulting mixture is filtered, the obtained solid is sequentially washed with acetonitrile and ethyl ether, and dried under vacuum. This solid, after being dissolved in methanol, was transformed into the corresponding hydroxide using an anionic exchange resin, with stirring, for 12 hours.

Example 2—Preparation of the ITQ-49 zeolite

To 28.69 g of a 0.7 M aqueous solution of 1,4-butanediyl-bis(tritertbutyl)phosphonium hydroxide, 1.9 g of $GeO_2$ and 13 g of tetraethyl orthosilicate are added. The mixture is kept under stirring at room temperature until the total evaporation of the ethanol formed during the hydrolysis of tetraethyl orthosilicate. Then, 1.67 g of HF (48%) are added and the enough amount of water to achieve a $H_2O/Si$ of 7.

The obtained gel was homogenized and transferred to teflon-coated steel autoclaves and they were put in a furnace with stirring at 125° C. for 16 days.

After the synthesis period, the solid is washed with distilled water at 85° C., it is centrifugated to separate the solid and dried at 100° C. for 12 hours.

The resulting solid has a X-ray diffraction diagram that contains the characteristic peaks of the ITQ-49 material.

Example 3—Preparation of the Zeolite ITQ-49 in its Calcined Form

A solid prepared according to example 2 was put in a muffle furnace and it was calcined in air at 700° C. for 5 hours to decompose the organic matter retained in its interior.

The resulting solid has a X-ray diffraction diagram that contains the characteristic peaks of the calcined ITQ-49 material.

Example 4—Preparation of the ITQ-49 Zeolite

To 28.69 g of a 0.7 M aqueous solution of 1,4-butanediyl-bis(tritertbutyl)phosphonium hydroxide, 1.4 g of $GeO_2$ and 14 g of tetraethyl orthosilicate are added. The mixture is kept under stirring at room temperature until the total evaporation of the ethanol formed during the hydrolysis of tetraethyl orthosilicate. Then, 1.67 g of HF (48%) are added and the enough amount of water to achieve a $H_2O/Si$ of 7.

The obtained gel was homogenized and transferred to teflon-coated steel autoclaves and they were put in a furnace with stirring at 125° C. for 16 days.

After the synthesis period, the solid is washed with distilled water at 85° C., it is centrifugated to separate the solid and dried at 100° C. for 12 hours.

The resulting solid has a X-ray diffraction diagram that contains the characteristic peaks of the ITQ-49 material.

Example 5—Refining of the Structure of ITQ-49 According Rietveld Method

Figure 4:
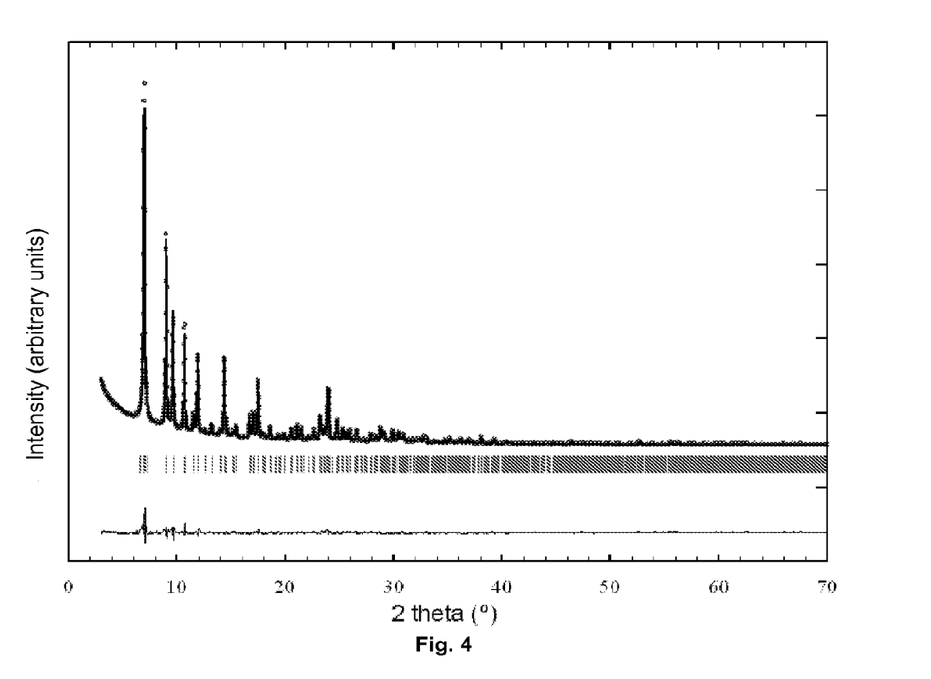
FIG. 4.—Rietveld refining of the X-ray diffraction diagram of a ITQ-49 sample, calcined at 923K, measured using the K alpha radiation of copper. The spots show the experimental diagram. The line along the spots shows the calculated diagram for the proposed structure. The difference between both is shown below. The vertical lines under the diagrams depict the positions of Bragg's reflections.

The structure of a sample of the zeolite ITQ-49 can be satisfactorily refined using Rietveld method applied to a X-ray diffraction diagram obtained from a sample prepared according to example 3. The matching between the experimental and the simulated diagrams is shown in FIG. 4. The space group, the refining parameters and the atomic positions of zeolite ITQ-49 are shown in Table 4.

TABLE 4

| Space group: |
| --- |
| l m m m |
| Parameters of unit cell: |
| a = 19.6007(8) angstroms |
| b = 18.3274(7) angstroms |
| c = 16.5335(6) angstroms |
| alpha = beta = gamma = 90° |

Atomic positions:

| Position | x | y | z | Ocupation |
| --- | --- | --- | --- | --- |
| Si1 | 0.2357(3) | 0.1189(3) | 0.1786(4) | 0.78(1) |
| Ge1 | 0.2357(3) | 0.1189(3) | 0.1786(4) | 0.22(1) |
| Si2 | 0.1640(3) | 0.3802(4) | 0.1797(4) | 0.77(1) |
| Ge2 | 0.1640(3) | 0.3802(4) | 0.1797(4) | 0.23(1) |
| Si3 | 0 | 0.1436(4) | 0.0908(5) | 0.89(1) |
| Ge3 | 0 | 0.1436(4) | 0.0908(5) | 0.11(1) |
| Si4 | 0.1389(4) | 0.2365(4) | 0.0960(4) | 0.91(1) |
| Ge4 | 0.1389(4) | 0.2365(4) | 0.0960(4) | 0.09(1) |
| Si5 | 0.0812(4) | ½ | 0.2575(5) | 0.83(1) |
| Ge5 | 0.0812(4) | ½ | 0.2575(5) | 0.17(1) |
| Si6 | 0.2487(4) | 0 | 0.4062(4) | 0.66(1) |
| Ge6 | 0.2487(4) | 0 | 0.4062(4) | 0.34(1) |
| Si7 | 0.1481(4) | 0 | 0.2636(4) | 0.78(1) |
| Ge7 | 0.1481(4) | 0 | 0.2636(4) | 0.22(1) |
| Si8 | 0.1806(4) | ½ | 0.4067(4) | 0.90(1) |
| Ge8 | 0.1806(4) | ½ | 0.4067(4) | 0.10(1) |
| Si9 | 0 | 0 | 0.2061(6) | 0.92(1) |
| Ge9 | 0 | 0 | 0.2061(6) | 0.08(1) |
| O1 | 0.2854(10) | 0.1493(7) | 0.2501(10) | 1.0 |
| O2 | 0.1695(7) | 0.0724(7) | 0.2126(11) | 1.0 |
| O3 | 0.2005(7) | 0.1898(7) | 0.1354(11) | 1.0 |
| O4 | 0.2665(7) | 0.0671(6) | 0.1070(8) | 1.0 |
| O5 | 0.0965(6) | 0.4320(7) | 0.1950(9) | 1.0 |
| O6 | 0.2144(8) | 0.4210(6) | 0.1153(9) | 1.0 |
| O7 | 0.1245(8) | 0.3199(6) | 0.1240(10) | 1.0 |
| O8 | 0 | 0.1096(11) | 0 | 1.0 |
| O9 | 0.0698(6) | 0.1891(8) | 0.1079(11) | 1.0 |
| O10 | 0 | 0.0663(7) | 0.1392(10) | 1.0 |
| O11 | 0.1468(13) | 0.2247(13) | 0 | 1.0 |
| O12 | 0.1151(8) | ½ | 0.3473(8) | 1.0 |
| O13 | 0 | ½ | 0.268(2) | 1.0 |
| O14 | 0.1749(7) | 0 | 0.3581(7) | 1.0 |
| O15 | 0.2169(11) | 0 | ½ | 1.0 |
| O16 | 0.0655(4) | 0 | 0.2650(10) | 1.0 |
| O17 | 0.1596(14) | ½ | ½ | 1.0 |

The invention claimed is:

1. A process for the preparation of a material, comprising at least the following steps:
    a) preparing a mixture containing $H_2O$, a source of fluoride ions, an oxide or
    another source of the tetravalent material Z and a structure directing agent (R), a source of the trivalent element X, an oxide or other source of the tetravalent material Y, wherein the synthesis mixture has a molar composition of oxides within the following ranges:

| | |
| --- | --- |
| $(YO_2 + ZO_2)/X_2O_3$ | higher than 2 |
| $H_2O/(YO_2 + ZO_2)$ | 1-50 |
| $R/(YO_2 + ZO_2)$ | 0.05-3.0 |
| $F^-/(YO_2 + ZO_2)$ | 0.01-3.0 |
| $ZO_2/YO_2$ | higher than 5 |
| $SiO_2/GeO_2$ | higher than 1 | b) maintaining the mixture at a temperature between 80 and 200° C. until crystals of the material are formed;
  c) recovering the crystalline material;
  wherein the microporous crystalline material has the following chemical composition:
  x $X_2O3$ : y$YO_2$: z$ZO_2$, wherein: X is a trivalent element selected from Al, B, Fe, In, Ga, Cr, or mixtures thereof; Y is a tetravalent element tetravalent selected from Ti, Sn, Zr, V or mixtures thereof; Z is a tetravalent element tetravalent selected from Si, Ge and mixtures thereof the value of (y+z)/x is comprised between 9 and infinity; the value of z/y is comprised between 10 and infinity; and an X-ray diagram shown in Table 3.

2. The process for the preparation of a material according to claim 1, wherein Z is Si, Ge or a mixture of both.

3. The process for the preparation of a material according to claim 1, wherein the strucure directing agent R is a compound that contains P.

4. The process for the preparation of a material according to claim 3, wherein R is an alkylphosphonium salt.

5. The process for the preparation of a material according to claim 4, wherein R is 1,4-butanediyl-bis(tritertbutyl) phosphonium hydroxide or one of its salts.

6. The process for the preparation of a material according to claim 1, that further comprises the calcination of the crystalline material obtained.

7. The process for the preparation of a material according to claim 6, wherein the calcination is carried out at a temperature between 200 and 1200° C.

8. The process for the preparation of a material according to claim 1, that further comprises one or more post-synthesis processes.

9. The process for the preparation of a material according to claim 8, wherein said post-synthesis treatment comprises at least:
a) suspending the material in a solution that contains at least a trivalent element X selected from the group consisting of Al, Ga, B, Cr, Fe, In and mixtures thereof;
b) recovering of the solid through filtration, centrifugation or any other technique for solids-liquids separation;
c) activating the material through calcination at temperatures higher than 200° C.

10. The process for the preparation of a material according to claim 9, wherein the solution is selected from the group consisting of an aqueous solution, an alcoholic solution, an organic solution and mixtures thereof.

11. The process for the preparation of a material according to claim 9, wherein the post-synthesis treatment is carried out at a temperature between 0 and 200° C.

12. Method of catalysing a reaction comprising subjecting the reagents to a catalyst comprising a microporous crystalline material, having a chemical composition:

$$xX_2O_3 : yYO_2 : zZO_2$$

wherein:
X is a trivalent element selected from Al, B, Fe, In, Ga, Cr, or mixtures thereof;
Y is a tetravalent element tetravalent selected from Ti, Sn, Zr, V or mixtures thereof;
Z is a tetravalent element tetravalent selected from Si, Ge and mixtures thereof; the value of (y+z)/x is comprised between 9 and infinity; the value of z/y is comprised between 10 and infinity; and
an X-ray diagram shown in Table 3.

13. Method of catalysing according to claim 12, wherein said material was obtained through a process comprising at least the following steps:
a) preparing a mixture containing H₂O, a source of fluoride ions, an oxide or another source of the tetravalent material Z and a structure directing agent (R), a source of the trivalent element X, an oxide or other source of the tetravalent material Y, wherein the synthesis mixture has a molar composition of oxides within the following ranges:

| | |
|---|---|
| (YO₂ + ZO₂)/X₂O₃ | higher than 2 |
| H₂O/(YO₂ + ZO₂) | 1-50 |
| R/(YO₂ + ZO₂) | 0.05-3.0 |
| F⁻/(YO₂ + ZO₂) | 0.01-3.0 |
| ZO₂/YO₂ | higher than 5 |
| SiO₂/GeO₂ | higher than 1 | b) maintaining the mixture at a temperature between 80 and 200° C. until crystals of the material are formed;
c) recovering the crystalline material.

14. Method of converting hydrocarbons comprising subjecting the hydrocarbons to a catalyst comprising the material described in claim 12.

15. Method of dewaxing hydrocarbons comprising subjecting the hydrocarbons to a catalyst comprising the material described in claim 12.

16. Method of converting hydrocarbons comprising subjecting the alcohols to a catalyst comprising the material described in claim 12.

17. Method for converting alcohols with less than four carbon atoms, into olefins comprising subjecting said alcohols to a catalyst comprising the material described in claim 12.

18. Method for removing nitrogenated pollutants in gaseous or liquid streams comprising subjecting said gaseous or liquid streams to a catalyst comprising the material described in claim 12.

19. Method for removing nitrogen oxides in gaseous streams comprising subjecting said gaseous stream to a catalyst comprising the material described in claim 12.

20. Method for removing nitrogen oxides in gaseous streams in the presence of reducing gases comprising subjecting said gaseous streams to a catalyst comprising the material described in claim 12.

21. Method for removing nitrogen oxides in gaseous streams in the presence of ammonia as a reducing agent comprising subjecting said gaseous streams to a catalyst comprising the material described in claim 12.

22. Method for removing nitrogen oxides in gaseous streams in the presence of hydrocarbons as reducing agents comprising subjecting said gaseous streams to a catalyst comprising the material described in claim 12.

23. Method of adsorbing a substance comprising putting said substance into contact with a microporous crystalline material, having a chemical composition:

$$xX_2O_3 : yYO_2 : zZO_2$$

wherein:
X is a trivalent element selected from Al, B, Fe, In, Ga, Cr, or mixtures thereof;
Y is a tetravalent element tetravalent selected from Ti, Sn, Zr, V or mixtures thereof;
Z is a tetravalent element tetravalent selected from Si, Ge and mixtures thereof; the value of (y+z)/x is comprised between 9 and infinity; the value of z/y is comprised between 10 and infinity; and
an X-ray diagram shown in Table 3, as an adsorbent.

24. Method of adsorbing a substance according to claim 23, wherein said material was obtained through a process comprising at least the following steps:
a) preparing a mixture containing H₂O, a source of fluoride ions, an oxide or another source of the tetravalent material Z and a structure directing agent (R), a source of the trivalent element X, an oxide or other source of the tetravalent material Y, wherein the synthesis mixture has a molar composition of oxides within the following ranges:

| | |
|---|---|
| (YO₂ + ZO₂)/X₂O₃ | higher than 2 |
| H₂O/(YO₂ + ZO₂) | 1-50 |
| R/(YO₂ + ZO₂) | 0.05-3.0 |
| F⁻/(YO₂ + ZO₂) | 0.01-3.0 |
| ZO₂/YO₂ | higher than 5 |
| SiO₂/GeO₂ | higher than 1 | b) maintaining the mixture at a temperature between 80 and 200.degree. C. until crystals of the material are formed;
c) recovering the crystalline material.

25. The method according to claim 23 wherein the adsorbent is a selective adsorbent and wherein CO₂ and methane are separated.

26. The method according to claim 23 wherein the adsorbent is a selective adsorbent and wherein propane and propene are separated.

27. The method according to claim 23 wherein the adsorbent is a selective adsorbent and wherein linear olefins are separated from the C4 fraction.

\* \* \* \* \*